(12) United States Patent
Buckley et al.

(10) Patent No.: US 10,065,052 B2
(45) Date of Patent: Sep. 4, 2018

(54) SKINCARE COMPOSITIONS

(75) Inventors: Carolyn Buckley, Hull (GB); Stuart Jackson, Hull (GB); Neil Kilcullen, Hull (GB); Diane Marie Pavis, Hull (GB)

(73) Assignee: Reckitt Benckiser Healthcare International Limited, Slough (GB)

( * ) Notice: Subject to any disclaimer, the term of this patent is extended or adjusted under 35 U.S.C. 154(b) by 0 days.

(21) Appl. No.: 13/384,233

(22) PCT Filed: Jul. 19, 2010

(86) PCT No.: PCT/GB2010/051170
§ 371 (c)(1),
(2), (4) Date: Mar. 2, 2012

(87) PCT Pub. No.: WO2011/007183
PCT Pub. Date: Jan. 20, 2011

(65) Prior Publication Data
US 2012/0189684 A1 Jul. 26, 2012

(30) Foreign Application Priority Data
Jul. 17, 2009 (GB) .................................. 0912481.9

(51) Int. Cl.
| | | |
|---|---|---|
| *A61Q 19/00* | (2006.01) | |
| *A61K 8/02* | (2006.01) | |
| *A61K 8/34* | (2006.01) | |
| *A61K 8/365* | (2006.01) | |
| *A61K 8/368* | (2006.01) | |
| *A61K 8/44* | (2006.01) | |
| *A61K 8/49* | (2006.01) | |
| *A61K 8/60* | (2006.01) | |
| *A61K 8/63* | (2006.01) | |
| *A61K 8/67* | (2006.01) | |
| *A61K 8/97* | (2017.01) | |
| *A61K 9/00* | (2006.01) | |
| *A61K 31/045* | (2006.01) | |
| *A61K 31/19* | (2006.01) | |
| *A61K 31/4166* | (2006.01) | |
| *A61K 31/60* | (2006.01) | |
| *A61K 36/185* | (2006.01) | |
| *A61K 45/06* | (2006.01) | |

(52) U.S. Cl.
CPC .......... *A61Q 19/008* (2013.01); *A61K 8/0208* (2013.01); *A61K 8/34* (2013.01); *A61K 8/365* (2013.01); *A61K 8/368* (2013.01); *A61K 8/442* (2013.01); *A61K 8/4913* (2013.01); *A61K 8/4946* (2013.01); *A61K 8/602* (2013.01); *A61K 8/63* (2013.01); *A61K 8/675* (2013.01); *A61K 8/97* (2013.01); *A61K 9/0014* (2013.01); *A61K 31/045* (2013.01); *A61K 31/19* (2013.01); *A61K 31/4166* (2013.01); *A61K 31/60* (2013.01); *A61K 36/185* (2013.01); *A61K 45/06* (2013.01); *A61Q 19/00* (2013.01); *A61K 2800/28* (2013.01)

(58) Field of Classification Search
CPC .... A61K 2300/00; A61K 31/19; A61K 31/60; A61K 36/185; A61K 2800/28; A61K 8/365; A61K 8/675; A61K 9/0014; A61Q 19/00; A61Q 19/008
See application file for complete search history.

(56) References Cited

U.S. PATENT DOCUMENTS

| | | | | |
|---|---|---|---|---|
| 5,482,710 A | * | 1/1996 | Slavtcheff | A61K 8/0212 424/65 |
| 5,520,919 A | * | 5/1996 | Lerner | 424/401 |
| 5,558,071 A | * | 9/1996 | Ward | F02P 3/02 123/598 |
| 5,843,998 A | | 12/1998 | Song | |
| 6,071,541 A | * | 6/2000 | Murad | A61K 8/22 424/616 |
| 6,579,851 B2 | * | 6/2003 | Goeke | A61K 38/26 514/11.7 |
| 8,263,097 B2 | * | 9/2012 | Jitpraphai et al. | 424/402 |
| 8,461,129 B2 | * | 6/2013 | Bolduc | A61L 15/28 127/49 |
| 2001/0019722 A1 | | 9/2001 | Fotinos | |
| 2002/0054918 A1 | | 5/2002 | Murad | |
| 2003/0180334 A1 | * | 9/2003 | Zhou et al. | 424/401 |

(Continued)

FOREIGN PATENT DOCUMENTS

| | | | | |
|---|---|---|---|---|
| EP | 2380657 A1 | * | 10/2011 | A61K 8/06 |
| GB | 2076286 A | * | 12/1981 | |

(Continued)

OTHER PUBLICATIONS

Gehring, W. "Nicotinic acid/niacinamide and the skin" Journal of Cosmetic Dermatology 2004, 3, 88-93 (abstract only).*
Barrett et al. (http://www.chelationwatch.org/reg/fda_warning.shtml), Sep. 26, 2008.*
"Viscosity" (http://www.viscopedia.com/basicsffactors-affecting-viscometry/) accessed Jan. 5, 2018, pp. 1-6 (Year: 2018).*
"pH" (http://www.phadjustment.com/pH.html) accessed Jan. 5, 2018, pp. 1-7 (Year: 2018).*

(Continued)

*Primary Examiner* — Andrew S Rosenthal
(74) *Attorney, Agent, or Firm* — Troutman Sanders LLP; Ryan Schneider; Chris Davis

(57) ABSTRACT

This invention relates to skincare compositions, in particular compositions effective in the treatment of acne vulgaris, and to methods of treatment of the skin that involve the application of such compositions, wherein the compositions comprise salicylic acid or a salt thereof in combination with at 2 actives selected from the group consisting of lactic acid or a salt thereof; glycyrrhizinic acid or a salt or derivative thereof; bisabolol; cetylhydroxyproline palmitamide; allantoin; niacinamide; and epilobium angustifolium extract.

14 Claims, No Drawings

(56) References Cited

U.S. PATENT DOCUMENTS

| | | | | |
|---|---|---|---|---|
| 2009/0148391 A1* | 6/2009 | Schmaus | ................ | A61K 8/347 |
| | | | | 424/59 |
| 2011/0028412 A1* | 2/2011 | Cappello | ............ | A61K 31/7004 |
| | | | | 514/25 |
| 2013/0084243 A1* | 4/2013 | Goetsch | ............. | C07K 16/2863 |
| | | | | 424/1.49 |
| 2013/0096073 A1* | 4/2013 | Sidelman | ........... | A61K 38/1709 |
| | | | | 514/21.6 |

FOREIGN PATENT DOCUMENTS

| | | |
|---|---|---|
| JP | H09500889 A | 1/1997 |
| JP | 2003530302 A | 10/2003 |
| JP | 2009522337 A | 6/2009 |
| WO | 20100058853 A1 | 5/2010 |

OTHER PUBLICATIONS

"Emulsion" (http://www.molecularrecipes.com/emulsions/emulsion-types/) accessed Jan. 5, 2018, pp. 1-7 (Year: 2018).*
Third Party Observation under Art 115 of EPC in related EP Publication No. EP2528577, dated Oct. 1, 2014.

\* cited by examiner

SKINCARE COMPOSITIONS

CROSS-REFERENCE TO RELATED APPLICATIONS

This application is a US National Stage of International Application No. PCT/GB2010/051170, filed 19 Jul. 2010, which claims the benefit of GB 0912481.9, filed 17 Jul. 2009, both herein fully incorporated by reference.

FIELD OF THE INVENTION

This invention relates to skincare compositions, in particular compositions effective in the treatment of acne vulgaris, and to methods of treatment of the skin that involve the application of such compositions.

BACKGROUND OF THE INVENTION

Acne vulgaris (acne) is a chronic inflammatory condition of the pilosebaceous units of the skin, which is particularly prevalent in adolescents. The condition generally causes the formation, on the skin, of comedones, red papules, pustules and sometimes cysts. This is unsightly and furthermore, if untreated, acne can lead to scarring of the skin. The major causes of acne are thought to be an increase in sebum production, an increased presence of propionibacterium acne (P. acne), blockage of the pilosebaceus duct and the production of inflammation.

Salicylic acid is known to be effective in the treatment of acne. It is a topical keratolytic agent that works by dissolving the intercellular cement that holds epithelial cells together. Salicylic acid is used in a variety of over-the-counter acne remedies.

In order to improve the efficacy of topical acne treatments, it is desired to formulate salicylic acid with one or more control agents to regulate the inflammatory effects sometimes observed, such as local skin peeling and discomfort such as burning and skin reddening.

BRIEF SUMMARY OF THE INVENTION

Surprisingly, it has now been found that skincare compositions comprising salicylic acid and at least two or more chosen actives have improved therapeutic efficacy in the treatment of acne. Said skincare compositions have both the ability to treat acne and reduce the appearance of redness on the skin.

Thus, according to a first aspect of the invention there is provided a skincare composition suitable for topical application to the skin, the composition comprising salicylic acid or a salt thereof, combined with at least 2 actives selected from the group consisting of:
  lactic acid or a salt thereof;
  glycyrrhizinic acid or a salt or derivatives thereof;
  bisabolol;
  cetylhydroxyproline palmitamide;
  allantoin;
  niacinamide; and,
  Canadian Willowherb (epilobium angustifolium) extract.

It has been found that this treatment provides advantages over existing acne treatments, particularly in tolerance of the acne treatment by the skin. It may have an effect in reducing the severity of the acne and hence any associated marks or scarring that can occur; furthermore, cutaneous irritation may be reduced. Other measures indicating advantages are the reduction in inflammation in the affected skin and/or a soothing effect. A synergistic association between the chosen combination of ingredients may provide that a composition may have lesser amounts of each individual ingredient Salicylic acid is preferably incorporated into the composition according to the invention as the free acid. However, the pH of the composition may, and generally will, be such that the salicylic acid exists in the composition in dissociated form. As the composition may well contain cationic counterions, the salicylic acid may then be thought of as being present in salt form. Alternatively, the salicylic acid may be incorporated into the composition already in salt form, eg as a salt with a Group I metal, such as sodium salicylate. As used herein, unless the context requires otherwise, any and all references to salicylic acid should be taken to encompass references to the acid and to dissociated forms and salts thereof.

The concentration of salicylic acid in the composition according to the invention is preferably at least 0.01 percent by weight, more preferably at least 0.1 percent, most preferably at least 0.5 percent and especially at least 1 percent by weight. The concentration of salicylic acid is preferably less than 10 percent, more preferably less than 5 percent, most preferably less than 4 percent and especially less than 3 percent by weight. The concentration of salicylic acid may therefore fall in the range 0.01 percent to 10 percent by weight, more preferably 0.1 percent to 5 percent, and most preferably 0.5 percent to 4 percent and especially 1 to 3 percent by weight. A particularly preferred concentration of salicylic acid is 2 percent by weight.

The concentration of lactic acid or salt thereof when present in the composition is at least 0.01 percent by weight, more preferably at least 0.1 percent by weight and most preferably at least 1 percent by weight; and is less than 10 percent by weight, more preferably less than 5 percent by weight, and most preferably less than 3 percent by weight.

The concentration of glycyrrhizinic acid or a salt or a derivative thereof when present in the composition is at least 0.01 percent by weight and is less than 2 percent by weight, more preferably less than 1 percent by weight, and most preferably less than 0.5 percent by weight.

The concentration of bisabolol when present in the composition is at least 0.001 percent by weight, more preferably at least 0.01 percent by weight and is less than 1 percent by weight, more preferably less than 0.5 percent by weight, The concentration of cetylhydroxyproline palmitamide when present in the composition is at least 0.001 percent by weight, more preferably at least 0.01 percent by weight and is less than 1 percent by weight, more preferably less than 0.5 percent by weight.

The concentration of allantoin when present in the composition is at least 0.01 percent by weight, more preferably at least 0.1 percent by weight and most preferably at least 0.2 percent by weight, and is less than 5 percent by weight, more preferably less than 2 percent by weight, and most preferably less than 1 percent by weight.

The concentration of niacinamide when present in the composition is at least 0.01 percent by weight, more preferably at least 0.1 percent by weight and most preferably at least 0.5 percent by weight, and is less than 10 percent by weight, more preferably less than 5 percent by weight.

The concentration of epilobium angustifolium extract when present in the composition is at least 0.01 percent by weight, and is less than 5 percent by weight, more preferably less than 1 percent by weight, and most preferably less than 0.5 percent by weight.

DETAILED DESCRIPTION OF PREFERRED EMBODIMENTS

In a particularly preferred embodiment of the present invention, there is provided a skincare composition comprising 0.1 to 5 wt % salicylic acid, or a salt thereof, in combination with at least 2 actives selected from the group consisting of:
 0.1 to 5 wt % lactic acid or a salt thereof;
 0.01 to 1 wt % glycyrrhizinic acid or a salt or derivative;
 0.001 to 1 wt % bisabolol;
 0.001 to 1 wt % cetylhydroxyproline palmitamide
 0.1 to 2 wt % allantoin;
 0.1 to 5 wt % niacinamide; and,
 0.001 to 1% epilobium angustifolium extract In a further particularly preferred embodiment of the present invention, there is provided a skincare composition comprising 1 to 3 wt % salicylic acid or a salt thereof; in combination with at least 2 actives selected from the group consisting of:
 1 to 3 wt % lactic acid or a salt thereof;
 0.01 to 0.5 wt % glycyrrhizinic acid or a salt or derivative
 0.02 to 0.5 wt % bisabolol;
 0.01 to 0.5 wt % cetylhydroxyproline palmitamide
 0.2 to 1 wt % allantoin;
 0.5 to 5 wt % niacinamide; and,
 0.01 to 0.5% epilobium angustifolium extract.

The composition is preferably prepared with a pH in the range 2.5 to 8.0, more preferably 3.0 to 7.0, and particularly a pH in the range 3.5 to 6.0, e.g. about pH 4.5 or pH 5.5.

A composition according to the invention may comprise one or more further topically active ingredients useful in skincare. Such active ingredients may include one or more of the following:

antimicrobial or antibacterial compounds, for example selected from the following: triclosan, neomycin, clindamycin, polymyxin, bacitracin, benzoyl peroxide, hydrogen peroxide, tetracylines such as doxycycline or minocycline, sulfa drugs such as sulfacetamide, penicillins, cephalosporins such as cephaiexin, and quinolones such as lomefloxacin, olfoxacin or trovafloxacin;

antiviral compounds, for example selected from acyclovir, tamvir, and penciclovir;

antifungal compounds, for example selected from the following: framesol, clotrimazole, ketoconazole, econazole, fluconazole, calcium or zinc undecylenate, undecylenic acid, butenafine hydrochloride, ciclopirox olaimine, miconazole nitrate, nystatin, sulconazole, and terbinafine hydrochloride; anti-inflammatory compounds, for example selected from the following: steroidal agents selected from hydrocortisone, fluocinolone acetonide, halcinonide, halobetasol propionate, clobetasol propionate, betamethasone dipropionate, betamethasone valerate, and triamcinolone acetonide, and non-steroidal anti-inflammatory agents selected from aspirin, ibuprofen, ketoprofen, naproxen, aloe vera gel, aloe vera, licorice extract, pilewort or zinc;

anthelmintic compounds, for example metronidazole.

The composition according to the invention may be formulated in numerous forms. However, the composition may often take the form of an aqueous or oily solution or surfactant wash or dispersion or emulsion or a gel. An emulsion may be an oil-in-water emulsion or a water-in-oil emulsion or microemulsion.

The oil phase of emulsions may comprise, but are not exclusive to: hydrocarbon oils such as paraffin or mineral oils; b) waxes such as beeswax or paraffin wax; c) natural oils such as sunflower oil, apricot kernel oil, shea butter or jojoba oil; d) silicone oils such as dimethicone, cyclomethicone or cetyldimethicone; e) fatty acid esters such as isopropyl palmitate, isopropyl myristate, dioctylmaleate, glyceryl oleate and cetostearyl isononanoate; f) fatty alcohols such as cetyl alcohol or stearyl alcohol and mixtures thereof (eg cetearyl alcohol); g) polypropylene glycol or polyethylene glycol ethers, eg PPG-14 butyl ether; or h) mixtures thereof, for example, the blend of waxes available commercially under the trade name Cutina (Henkel).

Emulsifiers used may be any emulsifiers known in the art for use in water-in-oil or oil-in-water emulsions or microemulsions. Known cosmetically acceptable emulsifiers may include: a) sesquioleates such as sorbitan sesquioleate, available commercially for example under the trade name Arlacel 83 (ICI), or polyglyceryl-2-sesquioleate; b) ethoxylated esters of derivatives of natural oils such as the polyethoxylated ester of hydrogenated castor oil available commercially for example under the trade name Arlacel 989 (ICI); c) silicone emulsifiers such as silicone polyols available commercially for example under the trade name ABIL WS08 (Th. Goldschmidt AG); d) anionic emulsifiers such as fatty acid soaps e.g. potassium stearate and fatty acid sulphates e.g. sodium cetostearyl sulphate available commercially under the trade name Dehydag (Henkel); e) ethoxylated fatty alcohols, for example the emulsifiers available commercially under the trade name Brij (ICI); f) sorbitan esters, for example the emulsifiers available commercially under the trade name Span (ICI); g) ethoxylated sorbitan esters, for example the emulsifiers available commercially under the trade name Tween (ICI); h) ethoxylated fatty acid esters such as ethoxylated stearates, glyceryl monostearates for example the emulsifiers available commercially under the trade name Myrj (ICI); i) ethoxylated mono-, di-, and tri-glycerides, for example the emulsifiers available commercially under the trade name Labrafil (Alfa Chem.); j) non-ionic self-emulsifying waxes, for example the wax available commercially under the trade name Polawax (Croda); k) ethoxylated fatty acids, for example, the emulsifiers available commercially under the trade name Tefose (Alfa Chem.)

l) methylglucose esters such as polyglycerol-3 methyl glucose distearate available commercially under the name Tegocare 450 (Degussa Goldschmidt); m) as well as polyacrylamide emulsifier systems for examples cream gel emulsifier under trade name Sepigel 305 (Seppic) or n) mixtures thereof.

Gels provided according to the invention may be aqueous or non-aqueous. Aqueous gels are preferred. The gel will contain a gelling agents in order to give sufficient viscosity to the gel. Suitable gelling agents may be hydroxypropyl guar or a copolymer of acryloyl dimethyl tauric acid (or a salt thereof), especially a copolymer of that monomer with another vinylic monomer. The salt may be a salt of a Group I alkali metal, but is more preferably an ammonium salt. Examples of suitable copolymer gelling agents are ammonium acryloyl dimethyl taurate/vinyl pyrrolidone copolymer, ammonium acryloyl dimethyl taurate/Beheneth-25 methacrylate copolymer, ammonium acryloyldimethyltaurate/vinyl formamide copolymer These materials are available from Clariant GmbH in the range of products under the trade name Aristoflex.

A variety of thickening agents may also be used according to the nature of the liquid carrier and the viscosity required. Thickeners that are water-soluble or hydrophilic are preferred, and examples include acrylic acid polymers, eg those available commercially under the trade name Carbopol (B.F. Goodrich), modified celluloses, eg hydroxypropylmethylcellulose or hydroxyethylcellulose available commercially under the trade name Natrosol (Hercules), alkylgalactomannans available under the trade name N-Hance, xanthan gum, cetyl alcohol and sodium chloride.

The amount of gelling and/or thickening agent in the composition will each preferably lie in the range 0.1 to 5 percent w/w, more preferably 0.5 to 5 percent w/w. Typically, the amount of gelling and/or thickening agent will each be less than 3 percent w/w, eg about 1 percent w/w or about 2 percent w/w.

The composition according to the invention preferably has a viscosity of from about 10,000 mPa·s to about 200,000 mPa·s, Viscosity may be measured using a Brookfield RVT viscometer equipped with a T bar C rotating at 5 rpm for 1 minute.

In many instances, it is preferred that the composition should comprise a chelating or sequestering agent, or other agent capable of complexation or other interaction with metal ions present in the composition. Such agents may improve the stability of the composition, and in particular may inhibit or prevent degradation of several ingredients (eg fragrance). Examples of chelating or sequestering agents include ethylenediamine tetraacetic acid and its salts, notably the dipotassium and especially the disodium salt.

In the case of solutions or dispersions, and gels, the composition will generally contain a solvent system or other continuous liquid phase. Such a system is preferably aqueous. However, mixed solvent systems may often be used with advantage. Such a mixed solvent system most preferably comprises water, in admixture with a co-solvent, most preferably a lower (eg $C_{1-6}$) alcohol, in particular ethanol and t-butyl alcohol.

Preferred aqueous systems comprise water in an amount of at least 25 percent by weight, more preferably at least 35 percent by weight, The upper limit of water will depend on the amounts of other ingredients incorporated in the composition so that the water may form the remainder of the composition up to 100 percent of the composition.

The composition may additionally comprise other components which will be well known to those skilled in the art. These include, for example:

a) Emollients—ingredients that help to maintain the soft, smooth and pliable appearance of skin. Such ingredients may function by their ability to remain on the surface of the skin or in the stratum corneum, and to act as lubricants, reducing or preventing flaking of the skin and improving the skin's appearance. Examples of emollients are isopropyl myristate, triglycerides of fatty acids eg lauric triglyceride or capric/caprylic triglyceride, such as the triglyceride available commercially under the trade name Miglyol 810 (Huls UK), and the polypropylene glycol ether of stearyl alcohol known as PPF-15 Stearyl Ether. Particularly preferred emollients are octyldodecanol and polysiloxane compounds, in particular those known as dimethicones.

b) Humectants or Moisturisers—ingredients intended to increase the water content of the top layers of the skin. Examples of such ingredients are glycerin, sorbitol, 1,3-butylene glycol and propylene glycol.

c) Surfactants—Surfactants may be used in compositions according to the invention as solubilisers, or as cleansing agents or foam boosters. Many different classes of surfactant may be suitable for inclusion in the composition according to the invention, and these will be readily apparent to those skilled in the art. Examples of suitable surfactants include anionic surfactants (eg sodium laureth sulphate, non ionic surfactants (eg cocoglucoside) cationic surfactants and/or amphoteric surfactants (eg cocoamidoproyl betaine). Polyethylene glycol ethers of alcohols such as isocetyl alcohol (eg Isoceteth-20), isostearyl alcohol (eg Isosteareth-20), cetyl alcohol (eg Ceteth-20), oleyl alcohol (eg Oleth-20) and cetearyl alcohol (eg Ceteareth-20).

d) Preservatives—ingredients which prevent or retard microbial growth and thus protect the composition from spoilage. Examples of preservatives include such as propylparaben, bronopol, sodium dehydroacetate, polyhexamethylenebiguanide hydrochloride, isothiazolone and diazolidinylurea.

e) Chelating agents or sequestering agents (sequestrants)—ingredients that have the ability to complex with and inactivate metallic ions in order to prevent their adverse effects on the stability or appearance of the composition, as described above. Examples of chelating agents are ethylenediamine tetraacetic acid and its salts, notably the dipotassium and especially the disodium or tetrasodium salt.

f) Abrasives—ingredients used to assist in the removal of unwanted tissue or foreign materials from the skin during application of the composition. Abrasives commonly comprise fine solid particles. Examples of suitable abrasives are polyethylene beads and aluminium oxide g) opacifying agents such as clays (eg kaolin and bentonite) as well as titanium dioxide.

h) pH adjusters—Ingredients used to control the pH of the composition. Examples of pH adjusters are inorganic salts such as sodium hydroxide, and organic bases such as triethanolamine and arginine.

i) Conditioning agents, for example distearyldimonium chloride.

j) Perfumes and colourings.

The composition according to the invention may be applied and left on the skin to have the desired therapeutic effect or it may be applied and then rinsed off, for example with water for surfactant based formulations. The composition may be applied with the aid of a fibrous material, for example a pad or a wipe.

According to another aspect of the invention, there is provided an article comprising a fibrous substrate, for example a material in the form of a pad or a wipe, impregnated with a skincare composition comprising salicylic acid or a salt thereof and at least 2 actives selected from the group consisting of lactic acid or a salt thereof; glycyrrhizinic acid or a salt or derivative thereof; bisabolol; cetylhydroxyproline palmitamide; allantoin; niacinamide; and, and epilobium angustifolium extract.

The fibrous material may be used to apply the composition onto the skin.

Suitable fibrous materials include cellulose or cotton fibres or a mixture thereof. The fibrous material may be impregnated with the composition as a wet wipe which is arranged for immediate use to apply the skincare composition of the present invention to the skin of the user. Alternatively, the fibrous material may be impregnated with the skincare composition and dried to form a dry wipe which requires to be wetted, for example with water, before it can be used.

According to a further aspect of the invention, there is provided method for the prophylactic or remedial treatment of acne, which method comprises the topical application to the skin of a patient of a skincare composition comprising salicylic acid or a salt thereof and at least 2 of the list comprising lactic acid or a salt thereof; glycyrrhizinic acid or a salt and their derivatives, bisabolol; cetylhydroxyproline palmitamide, allantoin, niacinamide. and epilobium angustifolium extract.

It will be appreciated that the method according to this aspect of the invention may be a therapeutic method, but will often be a primarily cosmetic method, the objective of which is to reduce or eliminate externally visible, and often unsightly, symptoms of acne vulgaris.

In a yet further aspect of the invention, there is provided the use of salicylic acid and at least 2 actives selected from the group consisting of lactic acid (or salts thereof); glycyrrhizinic acid (or salts or derivatives thereof); bisabolol; cetylhydroxyproline palmitamide; allantoin; niacinamide and epilobium angustifolium in the manufacture of a composition for the prophylactic or remedial treatment of acne by topical application of the composition to the skin.

The invention will now be described in greater detail, by way of illustration only, with reference to the following Examples.

Example 1: Serum

Example 2: Clear gel scrub

Example 3: Pearlised Gel Scrub

Example 4: Wash/mask

Example 5: Wash/mask

Example 6: Hydro alcoholic gel

Example 7: Cream Scrub

Example 8: Foaming Cream Scrub

The composition of each of these examples is shown fully in the following Tables 1-8.

Example 1

| Trade Name | % w/w in Formula | Function | EU INCI Name | % w/w in final formula |
|---|---|---|---|---|
| Purified water | QS 100 | Solvent | Aqua | to100% |
| Dissolvine Na2 | 0.05 | Sequestrant | Disodium EDTA | 0.05000 |
| Carbopol Ultrez 20 | 0.60 | Thickener | | 0.60000 |
| Veegum Ultra | 0.25 | Viscosity control (Thickener) | Magnesium Aluminum Silicate | 0.24250 |
| | | | CI 77891 | 0.00750 |
| Keltrol RD | 0.75 | Emulsion stabilising/ Viscosity control | Xanthan Gum | 0.75000 |
| Titanium dioxide Ph Eur | 0.20 | pigment | CI 77891 | 0.20000 |
| Eutanol G | 4.50 | Emollient | Octyldodecanol | 4.50000 |
| Arlamol HD | 1.50 | Emollient | Isohexadecane | 1.50000 |
| Silfar 100 | 2.00 | Skin conditioning | Dimethicone | 2.00000 |
| Salicylic acid | 2.00 | Keratolytic active | Salicylic Acid | 2.00000 |
| DENATURED ETHANOL SDA-40B 200 PROOF | 4.80 | Solvent | Alcohol Denat. (Ethyl Alcohol) | 4.79376 |
| | | Denaturant | Denatonium Benzoate | 0.00003 |
| | | Denaturant | Tert-Butyl alcohol | 0.00624 |
| SEPIGEL 305 | 2.0000 | Emulsion stabilising/ Viscosity control | Aqua | 0.71167 |
| | | | Polyacrylamide | 0.80000 |
| | | | C13-14 Isoparaffin | 0.37833 |
| | | | Laureth-7 | 0.11000 |
| CLEARLY FRESH FRAGRANCE | 0.2000 | Fragrance | Benzyl salicylate | 0.01844 |
| | | | Limonene | 0.00689 |
| | | | Parfum | 0.20000 |
| Sodium hydroxide 30% soln | 2.35 | Buffering agent | Aqua | 1.64500 |
| | | | Sodium hydroxide | 0.70500 |
| Purasal S/HQ 60 | 3.33 | moisturiser, skin lightener, anti-inflammatory | Aqua | 1.332 |
| | | | Sodium Lactate | 1.99800 |
| Symrepair | 0.50 | Anti-inflammatory, wound healing | Hexyldecanol | 0.42000 |
| | | | Bisabolol | 0.02500 |
| | | | Cetylhydroxyproline Palmitamide | 0.02500 |
| | | | Stearic Acid | 0.02500 |
| | | | *Brassica Campestris* Sterols | 0.00500 |
| Nicotinamide | 2.00 | skin lightening, anti-inflammatory | Niacinamide | 2.00000 |
| Dipotassium Glycyrrhizate | 0.10 | anti-inflammatory/ skin lightening | Dipotassium Glycyrrhizate | 0.10000 |
| Allantoin | 0.50 | anti-inflammatory | Allantoin | 0.50000 |
| Canadian Willowherb | 0.50 | Anti-inflammatory | *Epilobium angustifolium* | 0.0100 |

Example 2

| Trade Name | % w/w in Formula | Function | EU INCI Name | % w/w in final formula |
|---|---|---|---|---|
| Purified Water | To 100% | Solvent | Aqua | to 100% |
| Carbopol Ultrez 20 | 1.3 | Suspending Agent | Acrylates/C10-30 Alkyl Acrylate Crosspolymer | 1.3 |

-continued

| Trade Name | % w/w in Formula | Function | EU INCI Name | % w/w in final formula |
|---|---|---|---|---|
| Dissolvine Na2 | 0.1 | Sequestring Agent | Disodium EDTA | 0.1 |
| Glycerin | 8 | Humectant | Glycerin | 8 |
| Sorbitol | 2 | Humectant | Sorbitol | 1.40 |
|  |  |  | Aqua | 0.60 |
| Empicol ESB3/ M6 | 20 | Surfactant | Aqua | 14.37 |
|  |  |  | Sodium Laureth Sulfate | 5.40 |
|  |  |  | Sodium Hydroxide | 0.2 |
| Salicylic Acid | 2 | Active | Salicylic Acid | 2 |
| Cocoglucoside | 4.8 | Surfactant | Aqua | 2.352 |
|  |  |  | Cocoglucoside | 2.544 |
| Tego Betaine | 6.9 | Surfactant | Cocamidopropyl Betaine | 2.553 |
|  |  |  | Aqua | 3.726 |
|  |  |  | Sodium Chloride | 0.5037 |
| Perfume Clearly Fresh | 0.25 | Fragrance | Parfum | 0.25 |
|  |  |  | Limonene | 0.010329 |
|  |  |  | Benzyl Salicylate | 0.023055 |
| Sodium Hydroxide | 3 | pH Adjuster | Sodium Hydroxide | 0.9 |
|  |  |  | Aqua | 2.1 |
| Aluminium Oxide | 1.2 | Exfoliating Beads | Alumina | 1.2 |
| Cotahylene HO 1681 | 1 | Exfoliating Beads | Polyethylene | 1 |
| Gotalene Green | 0.2 | Exfoliating Beads | Polyethylene + COLOUR (TBD) | 0.2 |
| Genamin PQ 43 | 1 | Skin Conditioner | Aqua | 0.85 |
|  |  |  | Polyquaternium 43 | 0.15 |
| FD&C Yellow 6 | 0.001 | Colourant | CI 15985 | 0.001 |
| FD & C Blue 1 | 0.002 | Colourant | CI 42090 | 0.002 |
| Purasal S/HQ 60 | 3.33 | Moisturiser, Skin lightener, Anti-inflammatory | Aqua | 1.3320 |
|  |  |  | Sodium Lactate | 2.0000 |
| Nicotinamide | 2.00 | Skin lightening, Anti-inflammatory | Niacinamide | 2.0000 |
| Dipotassium Glycyrrhizate | 0.10 | Skin lightening, Anti-inflammatory | Dipotassium Glycyrrhizate | 0.1000 |
| SymRepair | 0.50 | Anri-inflammatory, Wound healing | Hexyldecanol | 0.42000 |
|  |  |  | Bisabolol | 0.02500 |
|  |  |  | Cetylhydroxyproline Palmitamide | 0.02500 |
|  |  |  | Stearic Acid | 0.02500 |
|  |  |  | *Brassica Campestris* Sterols | 0.00500 |
| Allantoin | 0.50 | Anti-inflammatory | Allantoin | 0.5000 |
| Canadian Willowherb | 0.50 | Anti-inflammatory | *Epilobium angustifolium* | 0.0100 |

Example 3

| Trade Name | % w/w in Formula | Function | EU INCI Name | % w/w in final formula |
|---|---|---|---|---|
| Purified Water | To 100% | Solvent | Aqua | To 100% |
| Carbopol Ultrez 20 | 1.4 | Suspending Agent | Acrylates/C10-30 Alkyl Acrylate Crosspolymer | 1.4 |
| Dissolvine Na2 | 0.1 | Sequestring Agent | Disodium EDTA | 0.1 |
| Glycerin | 8 | Humectant | Glycerin | 8 |
| Polyquaternium 43 | 0.7 | Conditioning Agent | Polyquaternium 43 | 0.105 |
|  |  |  | Aqua | 0.595 |
| Cocoglucoside | 4.8 | Surfactant | Aqua | 2.352 |
|  |  |  | Cocoglucoside | 2.544 |
| Tego Betaine | 6.9 | Surfactant | Cocamidopropyl Betaine | 2.553 |
|  |  |  | Aqua | 3.726 |
|  |  |  | Sodium Chloride | 0.5037 |
| Glycol Distearate | 2.5 | Pearlising Agent | Aqua | 1.625 |
|  |  |  | Glycol Distearate | 0.25 |
|  |  |  | Laureth-4 | 0.25 |
|  |  |  | Cocamidopropyl Betaine | 0.25 |
|  |  |  | Citric Acid | 0.125 |
| Empicol ESB3/ M6 | 26.7 | Surfactant | Aqua | 19.18395 |
|  |  |  | Sodium Laureth Sulfate | 7.209 |
|  |  |  | Sodium Hydroxide | 0.267 |

-continued

| Trade Name | % w/w in Formula | Function | EU INCI Name | % w/w in final formula |
|---|---|---|---|---|
| Salicylic Acid | 2 | Active | Salicylic Acid | 2 |
| Sodium Hydroxide | 3 | pH Adjuster | Sodium Hydroxide | 0.9 |
| | | | Aqua | 2.1 |
| Perfume Clearly Fresh | 0.2 | Fragrance | Parfum | 0.2 |
| | | | Benzyl Salicylate | 0.027666 |
| | | | Limonene | 0.006886 |
| Aluminium Oxide | 2.2 | Exfoliating | Alumina | 2.2 |
| Coathylene HO1681 | 2 | Exfoliating | Polyethylene | 2 |
| Gotalene Green | 0.2 | Exfoliating | Polyethylene (+CI TBD) | 0.2 |
| FD & C Yellow No.6 | 0.0015 | Colour | CI 15985 | 0.0015 |
| Blue No.1 FD&C | 0.00225 | Colour | CI 42090 | 0.00225 |
| Purasal S/HQ 60 | 3.33 | Moisturiser, Skin lightener, Anti-inflammatory | Aqua | 1.3320 |
| | | | Sodium Lactate | 2.0000 |
| Nicotinamide | 2.00 | Skin lightening, Anti-inflammatory | Niacinamide | 2.0000 |
| Dipotassium Glycyrrhizate | 0.10 | Skin lightening, Anti-inflammatory | Dipotassium Glycyrrhizate | 0.1000 |
| SymRepair | 0.50 | Anri-inflammatory, Wound healing | Hexyldecanol | 0.42000 |
| | | | Bisabolol | 0.02500 |
| | | | Cetylhydroxyproline Palmitamide | 0.02500 |
| | | | Stearic Acid | 0.02500 |
| | | | *Brassica Campestris* Sterols | 0.00500 |
| Allantoin | 0.50 | Anti-inflammatory | Allantoin | 0.5000 |
| Canadian Willowherb | 0.50 | Anti-inflammatory | *Epilobium angustifolium* | 0.0100 |

Example 4

| Trade Name | % w/w in Formula | Function | EU INCI Name | % w/w in final formula |
|---|---|---|---|---|
| Purified Water | to 100% | Solvent | Aqua | To 100% |
| Dissolvine Na2 | 0.01 | Sequestring Agent | Disodium EDTA | 0.0100 |
| Glycerin | 8.00 | Humectant | Glycerin | 8.0000 |
| Sodium Hydroxide 30% Solution | 1.25 | pH Adjuster | Aqua | 0.8750 |
| | | | Sodium Hydroxide | 0.3750 |
| Keltrol RD | 0.20 | Emulsion Stabiliser/Thickener | Xanthan Gum | 0.20 |
| Veegum Ultra | 0.20 | Emulsion Stabiliser/Thickener | Magnesium Aluminium Silicate | 0.194 |
| | | | CI77891 | 0.006 |
| Dehydol LS3 | 4.00 | Emulsifier/Surfactant | Laureth-3 | 4.0000 |
| Lanette 1665 | 8.00 | Emulsifier | Cetearyl Alcohol | 8.0000 |
| Salicylic Acid | 2.00 | Active | Salicylic Acid | 2.0000 |
| Hostopan SCI 85G | 10.00 | Surfactant | Sodium Cocoyl Isethionate | 8.5000 |
| | | Emollient/Emulsifying/Surfactant | Coconut Acid | 1.0000 |
| | | Antistatic/Hair conditioning/Cleansing | Sodium Isethionate | 0.4000 |
| | | Solvent | Aqua | 0.0010 |
| Empicol ESB3/M6 | 4.00 | Surfactant | Aqua | 2.8740 |
| | | | Sodium Laureth Sulfate | 1.080 |
| | | | Sodium Hydroxide | 0.040 |
| Tego glycinate 818M | 3.50 | Non-ionic surfactant | Sodium cocoamphoacetate | 1.05000 |
| | | | Aqua | 2.17000 |
| Kaolin | 6.00 | Clay | Hydrated Aluminium Silicate | 6.0000 |

-continued

| Trade Name | % w/w in Formula | Function | EU INCI Name | % w/w in final formula |
|---|---|---|---|---|
| Dry Flo PC | 2.00 | Oil Absorber | Aluminum Starch Octenylsuccinate | 2.0000 |
| Titanium Dioxide Ph Eur | 2.00 | Opacifier | CI77891 | 2.0000 |
| Perfume Clearly Fresh | 0.30 | Fragrance | Parfum | 0.3000 |
| | | | Benzyl Salicylate | 0.0277 |
| | | | Limonene | 0.0103 |
| Phenonip | 0.30 | Preservative | Phenoxyethanol | 0.2178 |
| | | | Ethyl paraben | 0.045 |
| | | | Propyl paraben | 0.012 |
| | | | Isobutyl paraben | 0.012 |
| | | | Butyl Paraben | 0.006 |
| | | | Methyl Paraben | 0.006 |
| Bentonite | 3.00 | Sebum Absorber | Bentonite | 3.0000 |
| Purasal S/HQ 60 | 3.33 | Moisturiser, Skin lightener, Anti-inflammatory | Aqua | 1.3320 |
| | | | Sodium Lactate | 2.0000 |
| Nicotinamide | 2.00 | Skin lightening, Anti-inflammatory | Niacinamide | 2.0000 |
| Dipotassium Glycyrrhizate | 0.10 | Skin lightening, Anti-inflammatory | Dipotassium Glycyrrhizate | 0.1000 |
| SymRepair | 0.50 | Anri-inflammatory, Wound healing | Hexyldecanol | 0.42000 |
| | | | Bisabolol | 0.02500 |
| | | | Cetylhydroxyproline Palmitamide | 0.02500 |
| | | | Stearic Acid | 0.02500 |
| | | | *Brassica Campestris* Sterols | 0.00500 |
| Allantoin | 0.50 | Anti-inflammatory | Allantoin | 0.5000 |
| Canadian Willowherb | 0.50 | Anti-inflammatory | *Epilobium angustifolium* | 0.0100 |

Example 5

| Trade Name | % w/w in Formula | Function | EU INCI Name | % w/w in final formula |
|---|---|---|---|---|
| Purified Water | To 100% | Solvent | Aqua | To 100% |
| Dissolvine Na2 | 0.05 | Sequestring Agent | Disodium EDTA | 0.05 |
| Glycerin | 7 | Humectant | Glycerin | 7.00 |
| Polyquaternium 43 | 0.3 | Conditioning Agent | Polyquaternium 43 | 0.045 |
| | | | Aqua | 0.255 |
| Keltrol RD | 0.3 | Emulsion Stabiliser/Thickener | Xanthan Gum | 0.30 |
| Veegum Ultra | 0.3 | Emulsion Stabiliser/Thickener | Magnesium Aluminium Silicate | 0.291 |
| | | | CI77891 | 0.009 |
| Butylene Glycol | 3 | Humectant | Butylene Glycol | 3.00 |
| Salicylic Acid | 2 | Active | Salicylic Acid | 2.00 |
| Empicol ESB3/M6 | 13.3 | Surfactant | Aqua | 9.5561 |
| | | | Sodium Laureth Sulfate | 3.591 |
| | | | Sodium Hydroxide | 0.133 |
| Cocoglucoside 50% | 3.2 | Surfactant | Aqua | 1.568 |
| | | | Cocoglucoside | 1.696 |
| Tego Betaine | 4.6 | Surfactant | Cocamidopropyl Betaine | 1.702 |
| | | | Aqua | 2.484 |
| | | | Sodium Chloride | 0.3358 |
| Phenonip | 0.3 | Preservative | Phenoxyethanol | 0.2178 |
| | | | Ethyl paraben | 0.045 |
| | | | Propyl paraben | 0.012 |
| | | | Isobutyl paraben | 0.012 |
| | | | Butyl Paraben | 0.006 |
| | | | Methyl Paraben | 0.006 |
| Sodium Hydroxide | 1.25 | pH Adjuster | Sodium Hydroxide | 0.38 |
| | | | Aqua | 0.88 |
| Kaolin | 8 | Clay | Hydrated Aluminium Silicate | 8.00 |
| Bentonite | 4 | Sebum Absorber | Bentonite | 4.0000 |
| Titanium Dioxide | 2 | Opacifier | CI77891 | 2.0000 |
| Fragrance Clearly Fresh | 0.2 | Fragrance | Parfum | 0.2000 |
| | | | Benzyl Salicylate | 0.0277 |
| | | | Limonene | 0.0069 |

-continued

| Trade Name | % w/w in Formula | Function | EU INCI Name | % w/w in final formula |
|---|---|---|---|---|
| Structure XL | 2 | Thickener/foam boosrter | Hydroxypropyl Starch Phosphate | 2.0000 |
| Structure Plus | 0.4 | Thickener | Acrylates/Aminoacrylates/C10-30 Alkyl PEG-20 Itaconate Copolymer | 0.0800 |
| | | | Aqua | 0.3160 |
| | | | Phenoxyethanol | 0.00288 |
| | | | Methyl Paraben | 0.00064 |
| | | | Ethyl Paraben | 0.00016 |
| | | | Propyl Paraben | 0.00008 |
| | | | Butyl Paraben | 0.00016 |
| | | | Isobutyl Paraben | 0.00008 |
| Blue No. 1 FD&C | 0.0018 | Colour | CI 42090 | 0.0018 |
| Purasal S/HQ 60 | 3.33 | Moisturiser, Skin lightener, Anti-inflammatory | Aqua | 1.332 |
| | | | Sodium Lactate | 1.998 |
| Nicotinamide | 2 | Skin lightening, Anti-inflammatory | Niacinamide | 2.000 |
| Dipotassium Glycyrrhizate | 0.1 | Skin lightening, Anti-inflammatory | Dipotassium Glycyrrhizate | 0.100 |
| SymRepair | 0.5 | Anri-inflammatory, Wound healing | Hexyldecanol | 0.420 |
| | | | Bisabolol | 0.025 |
| | | | Cetylhydroxyproline Palmitamide | 0.025 |
| | | | Stearic Acid | 0.025 |
| | | | *Brassica Campestris* Sterols | 0.005 |
| Allantoin | 0.5 | Anti-inflammatory | Allantoin | 0.5 |
| Canadian Willowherb | 0.50 | Anti-inflammatory | *Epilobium angustifolium* | 0.0100 |

Example 6

| Trade Name | % w/w in Formula | Function | EU INCI Name | % w/w in final formula |
|---|---|---|---|---|
| Purified water | Qs 100 | Solvent | Aqua | To 100% |
| Jaguar HP 105 | 1.20 | Thickener | Hydroxypropyl Guar | 1.12680 |
| | | | Aqua | 0.10800 |
| | | | Proteins | 0.01200 |
| | | | Ashes | 0.01920 |
| Timiron Silk Green | 0.20 | pearlising agent | CI77891 | 0.14200 |
| | | | Mica | 0.07400 |
| | | | Tin oxide | 0.00200 |
| Salicylic acid | 2.00 | Keratolytic active | Salicylic Acid | 2.00000 |
| Tween 20 | 2.50 | surfactant | Polysorbate 20 | 2.50000 |
| DENATURED ETHANOL | 27.00 | Solvent | Alcohol Denat. (Ethyl Alcohol) | 26.96490 |
| SDA-40B 200 PROOF | | Denaturant | Denatonium Benzoate | 0.00016 |
| | | Denaturant | Tert-Butyl alcohol | 0.03510 |
| Sodium hydroxide 30% soln | 2.00 | Buffering agent | Aqua | 1.40000 |
| | | | Sodium hydroxide | 0.60000 |
| CLEARLY FRESH FRAGRANCE | 0.2000 | Fragrance | Benzyl salicylate | 0.01844 |
| | | | Limonene | 0.00689 |
| | | | Parfum | 0.00000 |
| Purasal S/HQ 60 | 3.33 | moisturiser, skin lightener, anti-inflammatory | Aqua | 1.332 |
| | | | Sodium Lactate | 1.99800 |
| Symrepair | 0.50 | Anti-inflammatory, wound healing | Hexyldecanol | 0.42000 |
| | | | Bisabolol | 0.02500 |
| | | | Cetylhydroxyproline Palmitamide | 0.02500 |
| | | | Stearic Acid | 0.02500 |
| | | | *Brassica Campestris* Sterols | 0.00500 |
| Nicotinamide | 2.00 | skin lightening, anti-inflammatory | Niacinamide | 2.00000 |

-continued

| Trade Name | % w/w in Formula | Function | EU INCI Name | % w/w in final formula |
|---|---|---|---|---|
| Dipotassium Glycyrrhizate | 0.10 | anti-inflammatory/ skin lightening | Dipotassium Glycyrrhizate | 0.10000 |
| Allantoin | 0.50 | anti-inflammatory | Allantoin | 0.50000 |
| Canadian Willowherb | 0.50 | Anti-inflammatory | *Epilobium angustifolium* | 0.0100 |

Example 7

| Trade Name | % w/w in Formula | Function | EU INCI Name | % w/w in final formula |
|---|---|---|---|---|
| None | To 100% | Solvent | Aqua | To 100% |
| DISSOLVINE NA2 | 0.01000 | Sequestrant | Disodium EDTA | 0.01000 |
| Veegum ultra | 0.25000 | Emulsion stabiliser/ Thickener | Magensium Aluminium Silicate | 0.24250 |
| | | | CI77891 | 0.00750 |
| Keltrol RD | 0.50000 | Emulsion stabiliser/ Thickener | Xanthan Gum | 0.25 |
| Glycerin 99.7% USP | 3.00000 | Humectant | Glycerin | 3.00000 |
| Arlamole E | 2.00000 | Emollient | PPG-15 Stearyl Ether | 2.00000 |
| | | | Stearyl Alcohol | 3 |
| SALICYLIC ACID USP | 2.00000 | Keratolytic | Salicylic Acid | 2.00000 |
| Varisoft TA 100 | 1.50000 | Skin Conditioning | Distearyldimonium Chloride | 1.44000 |
| | | | Aqua | 0.06000 |
| | | | Sodium Chloride | 0.00225 |
| Tego Alkanol 16 | 1.00000 | Emollient | Myristyl Alcohol | 0.02500 |
| | | | Cetyl Alcohol | 1.00000 |
| Birj 721 | 0.50000 | Emulsifier | Steareth-21 | 0.49000 |
| | | | Aqua | 0.01000 |
| | | | Stearyl Alcohol | 0.03360 |
| | | | Arachidyl Alcohol | 0.08400 |
| | | | Behenyl Alcohol | 0.33600 |
| Tego Alkanol S2 | 0.25000 | Emilsifier | Steareth-2 | 0.25000 |
| Stepanol-WA extra PCA (SLS) | 3.57000 | Surfactant | Aqua | 2.53470 |
| | | | Sodium Lauryl Sulfate | 1.07100 |
| | | | Lauryl Alcohol | 0.04641 |
| | | | Sodium Sulfate | 0.02499 |
| Tego Betain A 16 | 6.67000 | Surfactant | Aqua | 3.60180 |
| | | | Cetyl Betaine | 2.13440 |
| | | | Alcohol | 0.66700 |
| | | | Sodium Chloride | 0.46690 |
| Clearly Fresh E0525379 | 0.35000 | Fragrance | Benzyl Salicylate | 0.03228 |
| | | | Limonene | 0.01205 |
| | | | Parfum | 0.35000 |
| Aluminium oxide F100 | 8.00000 | Abrasive agent | Alumina | 8.00000 |
| Purasal S/HQ 60 | 3.33 | Moisturiser, skin lightener, anti-inflammatory | Aqua | 1.333 |
| | | | Sodium Lactate | 2.00000 |
| Sym Repair | 0.50 | Anti-inflammatory, wound healing | Hexyldecanol | 0.42000 |
| | | | Bisabolol | 0.02500 |
| | | | Cetylhydroxyproline Palmitamide | 0.02500 |
| | | | Stearic Acid | 0.02500 |
| | | | *Brassica Campestris* Sterols | 0.00500 |
| Nicotinamide | 2.00 | Skin lightening, anti-inflammatory | Niacinamide | 2.00000 |
| Dipotassium Glycyrrhizate | 0.10 | Anti-inflammatory/ skin lightening | Dipotassium Glycyrrhizate | 0.10000 |
| Allantoin | 0.50 | anti-inflammatory | Allantoin | 0.50000 |
| Canadian Willowherb | 0.50 | Anti-inflammatory | *Epilobium angustifolium* | 0.0100 |

Example 8

| Trade Name | % w/w in Formula | Function | EU INCI Name | % w/w in final formula |
|---|---|---|---|---|
| None | To 100% | Solvent | Aqua | to 100% |
| DISSOLVINE NA2 | 0.05000 | Sequestrant | Disodium EDTA | 0.05000 |
| Carbopol ultrez 20 | 0.30000 | thickener | Acrylates/C10-30 Alkyl Acrylate Crosspolymer | 0.30000 |
| | | | Ethyl Acetate | 0.00135 |
| | | | Cyclohexane | 0.00135 |
| Glycerin 99.7% USP | 3.00000 | Humectant | Glycerin | 3.00000 |
| FD&C Blue No. 1 Granules | 0.00045 | Colorant | CI 42090 | 0.00042 |
| FD&C Yellow 6 | 0.00030 | Colorant | CI 15985 | 0.00030 |
| Hostapon SCI 85G | 10.00000 | Surfactant | Sodium Cocoyl Isethionate | 8.50000 |
| | | | Coconut Acid | 1.00000 |
| | | | Sodium Isethionate | 0.40000 |
| | | | Aqua | 0.10000 |
| Genapol LA030 | 3.00000 | Emulsifying/Surfactant | Laureth-3 | 3.00000 |
| Tego Alkanol 16 | 6.00000 | Emollient | Myristyl Alcohol | 0.15000 |
| | | | Cetyl Alcohol | 6.00000 |
| SALICYLIC ACID USP | 2.00000 | Keratolytic | Salicylic Acid | 2.00000 |
| Empicol ESB3/M6 | 9.26000 | Anionic Surfactant | Sodium Laureth Sulfate | 2.54650 |
| | | | Aqua | 6.80610 |
| Sodium Hydroxide 30% | 1.25000 | Buffering agent | Sodium hydroxide | 0.37500 |
| | | | Aqua | 1.12500 |
| Tego glycinate 818M | 6.13000 | Non-ionic surfactant | Sodium cocoamphoacetate | 1.83900 |
| | | | Aqua | 3.80060 |
| Clearly Fresh E0525379 | 0.35000 | Fragrance | Benzyl Salicylate | 0.03228 |
| | | | Limonene | 0.01205 |
| | | | Parfum | 0.35000 |
| Genamin PQ 43 | 0.10000 | Conditioning agent | Polyquaternium 43 | 0.08500 |
| | | | Aqua | 0.01500 |
| Aluminium oxide F100 | 8.00000 | Abrasive agent | Alumina | 8.00000 |
| Parabeads green | 0.50000 | Exfolliant | Mycrocristalline wax | 0.48995 |
| | | | CI 77289 | 0.01000 |
| | | | Tocopherol (Processing aid) | 0.00005 |
| Purasal S/HQ 60 | 3.33 | Moisturiser, skin lightener, anti-inflammatory | Aqua | 1.33300 |
| | | | Sodium Lactate | 2.00000 |
| SymRepair | 0.50 | Anti-inflammatory, wound healing | Hexyldecanol | 0.42000 |
| | | | Bisabolol | 0.02500 |
| | | | Cetylhydroxyproline Palmitamide | 0.02500 |
| | | | Stearic Acid | 0.02500 |
| | | | *Brassica Campestris* Sterols | 0.00500 |
| Nicotinamide | 2.00 | Skin lightening, anti-inflammatory | Niacinamide | 2.00000 |
| Dipotassium Glycyrrhizate | 0.10 | Anti-inflammatory/skin lightening | Dipotassium Glycyrrhizate | 0.10000 |
| Allantoin | 0.50 | anti-inflammatory | Allantoin | 0.50000 |
| Canadian Willowherb | 0.50 | Anti-inflammatory | *Epilobium angustifolium* | 0.0100 |

Example 9

| Supplier | Trade Name | % w/w in Formula | Function | EU INCI Name | % w/w in raw material | % w/w in final formula |
|---|---|---|---|---|---|---|
| | Purified water | 73.12 | Solvent | Aqua | 100 | 73.12 |
| Akzo Nobel | Dissolvine Na2 | 0.05 | Sequestrant | Disodium EDTA | 100 | 0.05 |

-continued

| Supplier | Trade Name | % w/w in Formula | Function | EU INCI Name | % w/w in raw material | % w/w in final formula |
|---|---|---|---|---|---|---|
| Noveon | Carbopol Ultrez 20 | 0.60 | Thickener | Acrylates/C10-30 Alkyl Acrylate crosspolymer | 100 | 0.6 |
| RT Vanderbilt Co | Veegum Ultra | 0.25 | Viscosity control (Thickener) | Magnesium Aluminum Silicate | 97 | 0.2425 |
|  |  |  |  | Titanium Dioxide | 3 | 0.0075 |
| CP Kelco | Keltrol RD | 0.60 | Emulsion stabilising Viscosity control | Xanthan Gum | 100 | 0.6 |
| sensient | Titanium dioxide Ph Eur | 0.20 | pigment | Titanium Dioxide | 100 | 0.2 |
| Cognis | Eutanol G | 4.50 | Emollient | Octyldodecanol | 100 | 4.5 |
| Croda | Arlamol HD | 1.50 | Emollient | Isohexadecane | 100 | 1.5 |
| Wacker | Silfar 100 | 2.00 | Skin conditioning | Dimethicone | 100 | 2.0 |
| Rhodia | Salicylic acid | 2.00 | Keratolytic active | Salicylic Acid | 100 | 2.0 |
| MGP Ingredientes | Denatured Ethanol | 4.80 | Solvent | Alcohol Denat. (Ethyl Alcohol) | 99.87 | 4.79376 |
| Seppic | SEPIGEL 305 | 2.0 | Emulsion stabilising/ Viscosity control | Water | 35.583 | 0.71167 |
|  |  |  |  | Polyacrylamide | 40 | 0.8 |
|  |  |  |  | C13-14 Isoparaffin | 18.917 | 0.37833 |
|  |  |  |  | Laureth-7 | 5.5 | 0.11 |
| Mane | CLEARLY FRESH FRAGRANCE | 0.20 | Fragrance | Benzyl salicylate | 9.222 | 0.01844 |
|  |  |  |  | Limonene | 3.443 | 0.00689 |
|  |  |  |  | Fragrance | 100 | 0.2 |
| Univar | Sodium hydroxide 30% soln | 2.35 | Buffering agent | Water | 70 | 1.645 |
|  |  |  |  | Sodium hydroxide | 30 | 0.705 |
| Purac | Purasal S/HQ 60 | 3.33 | moisturiser, skin lightener, anti-inflammatory | Water | 40 | 1.332 |
|  |  |  |  | Sodium Lactate | 60 | 1.998 |
| Symrise | Symrepair | 0.50 | Anti-inflammatory, wound healing | Hexyldecanol | 84 | 0.42 |
|  |  |  |  | Bisabolol | 5.0 | 0.025 |
|  |  |  |  | Cetylhydroxyproline Palmitamide | 5.0 | 0.025 |
|  |  |  |  | Stearic Acid | 5.0 | 0.025 |
|  |  |  |  | *Brassica Campestris* Sterols | 1.0 | 0.005 |
| Rona (S Black) | Nicotinamide | 2.00 | skin lightening, anti-inflammatory | Niacinamide | 100 | 2.0 |
| Jan Dekkar (Maururzen) | Dipotassium Glycyrrhizate | 0.05 | anti-inflammatory/ skin lightening | Dipotassium Glycyrrhizate | 100 | 0.05 |

Example 10

| Supplier | Trade Name | % w/w in Formula | Function | EU INCI Name | % w/w in raw material | % w/w in final formula |
|---|---|---|---|---|---|---|
| — | Purified Water | 56.55685 | Solvent | Aqua | 100 | 56.55685 |
| BASF | Trilon BD | 0.05 | Sequestring Agent | Disodium EDTA | 100 | 0.050 |
| P & G | Glycerin | 5.00 | Humectant | Glycerin | 100 | 5.00 |
| CP Kelco | Keltrol RD | 1.00 | Emulsion stabiliser/ Thickener | Xanthan Gum | 100 | 1.00 |
| Rhodia | Salicylic Acid | 2.00 | Active | Salicylic Acid | 100 | 2.00 |
| Huntsman | Empicol ESB3/M6 | 10.70 | Surfactant | Sodium Laureth Sulfate | 27.5 | 2.9425 |
|  |  |  |  | Aqua | 73.5 | 7.8645 |
| Cognis | Cocoglucoside 50% | 1.00 | Surfactant | Aqua | 49 | 0.490 |
|  |  |  |  | Cocoglucoside | 53 | 0.530 |
| Evonik | Tego Betaine | 1.31 | Surfactant | Cocamidopropyl Betaine | 37 | 0.485 |

-continued

| Supplier | Trade Name | % w/w in Formula | Function | EU INCI Name | % w/w in raw material | % w/w in final formula |
|---|---|---|---|---|---|---|
| | | | | Aqua | 54 | 0.707 |
| | | | | Sodium Chloride | 7.3 | 0.0956 |
| Brenntag | Sodium Hydroxide | 1.20 | pH Adjuster | Sodium Hydroxide | 30 | 0.36 |
| | | | | Aqua | 70 | 0.840 |
| Brenntag | Kaolin | 6.00 | Clay | Hydrated Aluminium Silicate | 100 | 6.00 |
| Brenntag | Bentonite | 6.00 | Sebum Absorber | Bentonite | 100 | 6.00 |
| Huntsman | Titanium Dioxide | 3.00 | Opacifier | CI77891 | 100 | 3.00 |
| Mane | Fragrance Clearly Fresh | 0.30 | Fragrance | Benzyl Salicylate | 9.222 | 0.03 |
| | | | | Limonene | 3.443 | 0.01 |
| | | | | Parfum | 100 | 0.30 |
| Sun Chem | Blue No. 1 | 0.0026 | Colour | CI 42090 | 100 | 0.00260 |
| Sun Chem | Yellow No.6 | 0.00055 | Colour | CI 15985 | 100 | 0.00055 |
| Purac | Purasal S/HQ 60 | 3.33 | Moisturiser, Skin lightener, Anti-inflammatory | Aqua | 40 | 1.33 |
| | | | | Sodium Lactate | 60 | 2.00 |
| Rona (S Black) | Nicotinamide | 2.00 | Skin lightening, Anti-inflammatory | Niacinamide | 100 | 2.00 |
| Jan Dekkar (Mauruzen) | Dipotassium Glycyrrhizaet | 0.05 | Skin lightening, Anti-inflammatory | Dipotassium Glycyrrhizate | 100 | 0.05 |
| Symrise | SymRepair | 0.50 | Anri-inflammatory, Wound healing | Hexyldecanol | 84 | 0.42 |
| | | | | Bisabolol | 5 | 0.03 |
| | | | | Cetylhydroxyproline Palmitamide | 5 | 0.03 |
| | | | | Stearic Acid | 5 | 0.03 |
| | | | | *Brassica Campestris* Sterols | 1 | 0.01 |

Example 11—In Vitro Testing (Epiderm Skin Model)

| Material | MTT < 95% | IL-6 no PMA (pg/ml) | IL-6 + PMA (pg/ml) | TNFα no PMA (pg/ml) | TNFα + PMA (pg/ml) | IL-8 no PMA (pg/ml) | IL-8 no PMA (pg/ml) |
|---|---|---|---|---|---|---|---|
| Negative Control value | | −0.371 | | 63.64 | | 996.8 | |
| Positive control (hydrocortisone) | | −4.358 | | −0.378 | | 48.5 | |
| Nicotinamide (NA) | 96.8 | −4.294 | −2.712 | −0.171 | 40.202 | 47.54 | 1383.235 |
| Dipotassium glycyrrhizinate (GLYR) | 93.7 | −1.781 | 7.591 | −0.636 | 78.48 | 44.413 | 995.622 |
| Sodium Lactate (SLA) | 99.1 | 4.909 | 22.6 | 0.882 | 92.434 | 104.549 | 1368.319 |
| Symrepair (SYM) | 101.3 | −4.231 | 1.512 | −0.687 | 72.343 | 17.767 | 735.562 |
| Salicylic acid (SCA) | 103.2 | −1.445 | 6.159 | −0.068 | 12.265 | 72.757 | 362.253 |
| SCA + NA | 106.3 | −4.231 | −3.407 | −0.481 | 5.535 | 38.963 | 392.411 |
| GLYR + SCA + NA | 105.6 | −3.153 | −0.877 | −0.274 | 4.541 | 61.931 | 412.226 |
| NA + GLYR +SLA | 113.7 | −2.837 | 1.955 | −0.088 | 52.327 | 62.91 | 2513.021 |
| Example 9 (NA + GLYR + SLA + SCA) | 99.7 | −1.192 | 1.267 | −0.171 | 9.802 | 88.766 | 938.475 |

The purpose of the in vitro testing was to evaluate the potential anti-inflammatory action of compositions according to the present invention.

In vitro tests were carried out as follows:

take an irritant treated EpiDerm™ skin model. Initial inflammation was measured by the cytokine release after exposure to a single dose of irritant.

apply test compositions to the irritant treated EpiDerm skin anti-inflammatory potential was then measured by reduction in cytokine release specifically, the levels of cytokines TNF-α, IL-6 and IL-8 were measured to give a picture of the performance of the product across the lifecycle of an acne event or related skin inflammation.

Experimental design follows standard procedures, using phorbol-12-myristate 13-acetate (PMA) as irritant. Test samples were applied by pipette as solutions to the Epiderm tissue, and each sample was tested in triplicate against positive and negative controls. Anti-inflammatory activity measured by relative decrease in cytokine release in irritant-treated tissue compared to non-irritant treated tissue.

The separate active components of an example according to the invention were tested, along with some combinations in pairs and one combination lacking the salicylic acid.

Where these actives were applied, they were in the same w/w ratio as in the example composition, example 9. The data shown in the table are the cytokine release values in pg/ml, wherein a lower figure shows a lower release rate of cytokines i.e. a lower inflammation.

It will be seen that salicylic acid alone acts inter alia as an anti-inflammatory, but that unexpectedly it also acts with the combination of ingredients in the example according to the invention to reduce significantly the inflammatory behaviour of each of these ingredients. This synergistic behaviour is totally unexpected and permits the formulation of products according to the invention such as the one tested which have a broad range of active ingredients to deal with traumas arising from every stage in the lifecycle of a specific acne event or related skin inflammation.

The invention claimed is:

1. A skincare composition suitable for topical application to the skin, the composition consisting of:
   salicylic acid or a salt thereof in a concentration of 2 wt %;
   glycyrrhizinic acid or a salt thereof in a concentration of 0.05 wt %;
   cetylhydroxyproline palmitamide in a concentration of 0.025 wt %;
   lactic acid or a salt thereof in a concentration of 1.998 wt %;
   bisabolol in a concentration of 0.025 wt %;
   niacinamide in a concentration of 2 wt %;
   allantoin in a concentration of at least 0.01 percent by weight to less than 5 percent by weight;
   a chelating agent in a concentration of 0.01 wt % to 0.1 wt %;
   a gelling/thickening agent in a concentration of 0.1 wt % to 5 wt %;
   an emulsifier in a concentration of 0.75 wt % to 12 wt %;
   a mixed solvent system comprising water and a co-solvent wherein the co-solvent is present in a concentration of 0 wt % to about 5 wt % and the water forms the remainder of the composition;
   an emollient in a concentration of 0 wt % to 8 wt %;
   a humectant or moisturizer in a concentration of 0 wt % to 10 wt %;
   a surfactant in a concentration of 0 wt % to about 38 wt %;
   a preservative in a concentration of 0 wt % to 0.3 wt %;
   an abrasive in a concentration of 0 wt % to 8.5 wt %;
   an opacifying agent in a concentration of 0 wt % to 15 wt %;
   a pH adjuster in a concentration of 0 wt % to 3 wt %;
   a conditioning agent in a concentration of 0 wt % to 1.5 wt %;
   a perfume in a concentration of 0 wt % to 0.35 wt %; and
   a coloring in a concentration of 0 wt % to 0.00315 wt %,
   wherein the composition has a viscosity of from about 10,000 mPa/s to about 200,000 mPa/s.

2. The composition as claimed in claim 1, wherein the pH is in the range from 3.5 to 6.0.

3. The composition as claimed in claim 1 having the form of one of an aqueous solution surfactant wash, an oily solution surfactant wash, a dispersion, an emulsion, or a gel.

4. The composition as claimed in claim 3 having the form of an emulsion comprising an oil-in-water emulsion.

5. The composition as claimed in claim 3 having the form of a gel comprising an aqueous gel.

6. An article comprising a fibrous substrate impregnated with a skincare composition according to claim 1.

7. The article as claimed in claim 6, the fibrous substrate selected from the group consisting of cellulose fibers, cotton fibers, and a mixture thereof.

8. A method for the treatment of acne comprising the topical application to the skin of a patient of the skincare composition according to claim 1.

9. The method as claimed in claim 8, which is a cosmetic method.

10. The method as claimed in claim 8, which is a therapeutic method.

11. The use of the composition according to claim 1 in a composition for the treatment of acne by topical application of the composition to the skin.

12. A method for reducing irritancy associated with the topical application of a skincare composition according to claim 1.

13. A cosmetic method for improving the appearance of skin afflicted by acne lesions comprising reducing the redness of lesions by the topical application of a skincare composition according to claim 1.

14. The composition as claimed in claim 3 having the form of an emulsion selected from the group consisting of an oil-in-water emulsion, a water-in-oil emulsion, and a microemulsion.

* * * * *